United States Patent [19]

Smiley

[11] 4,211,722

[45] Jul. 8, 1980

[54] FORMALDEHYDE STABILIZATION OF ACRYLONITRILE AGAINST COLOR

[75] Inventor: Robert A. Smiley, Wilmington, Del.

[73] Assignee: E. I. Du Pont de Nemours & Co., Wilmington, Del.

[21] Appl. No.: 18,405

[22] Filed: Mar. 7, 1979

[51] Int. Cl.$^2$ .................. C07C 120/14; C07C 121/32
[52] U.S. Cl. .............................. 260/465.3; 260/465.9; 548/235
[58] Field of Search ........................ 260/465.3, 465.9

[56] References Cited

U.S. PATENT DOCUMENTS

| | | | |
|---|---|---|---|
| 2,656,376 | 10/1953 | Martino | 260/465.9 |
| 2,676,977 | 4/1954 | Carpenter | 260/465.9 |
| 2,878,205 | 3/1959 | Holmes et al. | 260/32.6 |
| 2,878,231 | 3/1959 | Campbell et al. | 260/32.6 |
| 3,009,943 | 11/1962 | Hadley et al. | 260/465.3 |
| 3,262,966 | 7/1966 | Higgins, Jr. et al. | 260/465.9 |
| 3,496,212 | 2/1970 | Davison et al. | 260/465.8 R |
| 3,524,875 | 8/1970 | Hadley et al. | 260/465.9 X |
| 3,541,131 | 11/1970 | Darcas et al. | 260/465.3 |
| 3,574,687 | 4/1971 | Darcas et al. | 260/465.3 X |
| 3,686,263 | 8/1972 | Maute | 260/465.9 |
| 3,697,576 | 10/1972 | Allirot et al. | 260/465.9 X |
| 3,758,545 | 9/1973 | Pounder et al. | 260/465.8 R |

FOREIGN PATENT DOCUMENTS 928406 5/1955 Fed. Rep. of Germany .... 260/465.8 R

OTHER PUBLICATIONS

Bruson, Organic Reactions, vol. 5, (1949), p. 93.
Brown et al., J. Chem. Soc., (1969), pp. 270–276.
Walker, "Formaldehyde", A.C.S. Monograph 120, (1953); Reinhold Publ. Co., N.Y., pp. 479–480.
Walker, "Formaldehyde", A.C.S. Monograph 159, (1964), Reinhold Publ. Co., N.Y., pp. 636–637.
Kirk–Othmer, "Ecyclopedia of Chemical Technology", 3rd ed., vol. 1, (1978), Wiley–Interscience, N.Y., pp. 417–426.
Cornforth et al., J. Chem. Soc., (1947), pp. 96–102.
Wiley, Chem. Reviews, (1946), pp. 401–442.

*Primary Examiner*—Joseph Paul Brust
*Attorney, Agent, or Firm*—James A. Costello

[57] ABSTRACT

A process for stabilizing acrylonitrile against color comprising adding thereto a color-inhibiting amount of formaldehyde. A solution composition comprising acrylonitrile and a color-inhibiting amount of formaldehyde.

10 Claims, 1 Drawing Figure

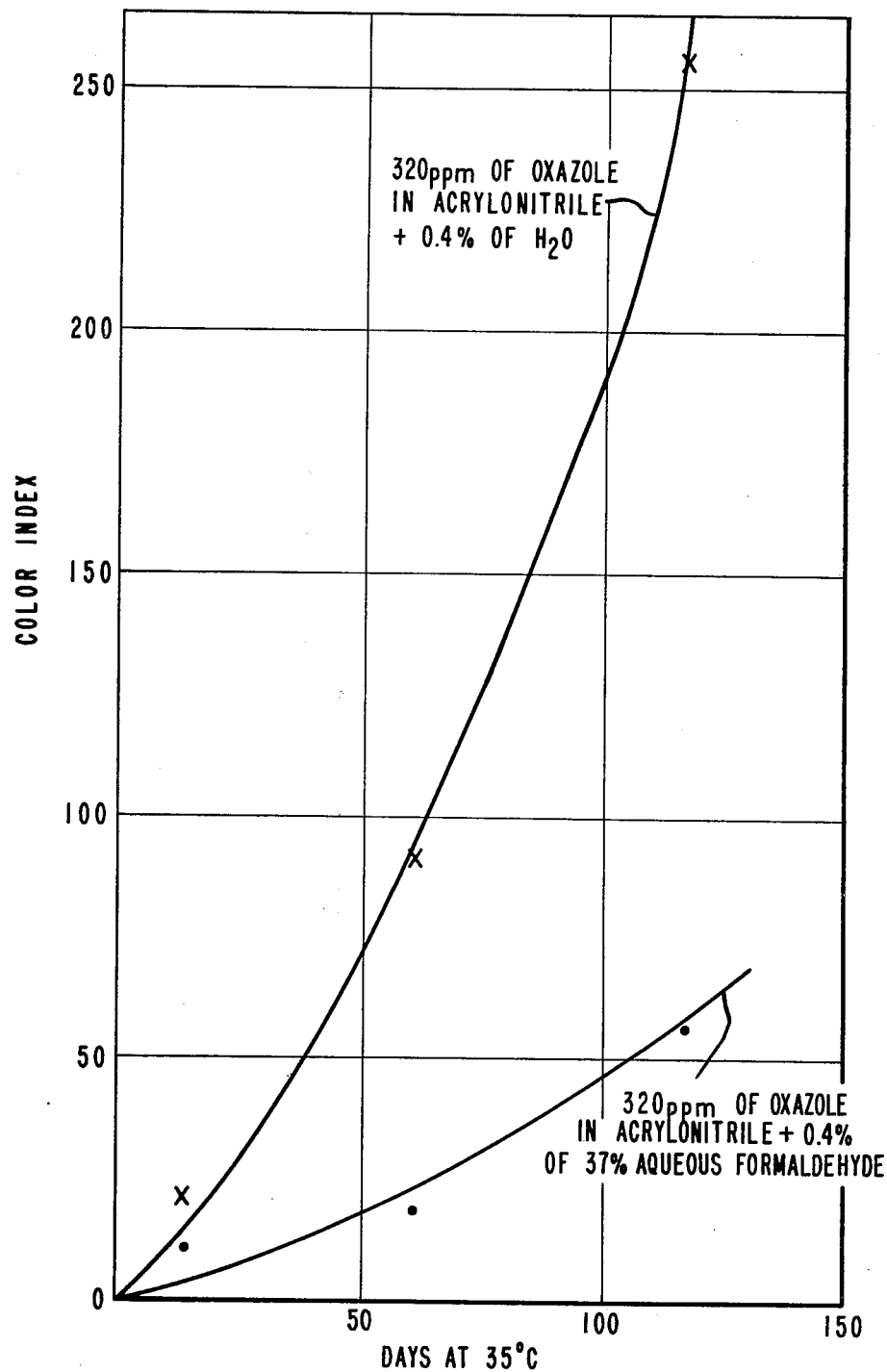

FORMALDEHYDE STABILIZATION OF ACRYLONITRILE AGAINST COLOR

This invention concerns inhibiting the formation of color in acrylonitrile monomer by adding formaldehyde thereto.

Oxazole is a known color-forming impurity in acrylonitrile monomer. The art has removed oxazole from acrylonitrile by employing ion-exchange resins; see U.S. Pat. No. 3,541,131 and U.S. Pat. No. 3,574,687. Adsorbents such as silica, clay and alumina have been taught to remove oxazole; see U.S. Pat. No. 3,697,576.

It has been taught that water, in the proper concentration, will stabilize acrylonitrile against color; see U.S. Pat. No. 2,676,977. Decolorizing carbon plus a cation exchange material plus water has also been suggested; see U.S. Pat. No. 622,097.

Inorganic cadmium salts have been taught to complex with the oxazole; see U.S. Pat. No. 3,522,268. Benzenesulfonic acid has been suggested as a decolorant during solution polymerization of acrylonitrile; see Japan Pat. No. 74/11,272.

Formaldehyde has been employed as a stabilizer against color formation in several materials, including acrylonitrile copolymers; see Walker, "Formaldehyde", ACS Monograph 159, Reinhold Publishing Co., N.Y., 1964.

SUMMARY OF THE INVENTION

This invention concerns the inhibition of color in oxazole-containing acrylonitrile, ACRN; especially ACRN prepared by the reaction of propylene, ammonia and oxygen. The acrylonitrile is stabilized against color formation by adding thereto an effective color-inhibiting amount of formaldehyde. This invention also concerns a composition of matter comprising a solution of ACRN and a color-inhibiting amount of formaldehyde.

The color-inhibiting effect of formaldehyde is believed to be attributable to the reaction of formaldehyde with oxazole. If so, the reaction could decrease the opportunity for oxazole to react with the ACRN to form color. Although the exact mode of action is not known with certainty, even small amounts of formaldehyde will inhibit color formation to some extent. Thus, all ACRN solutions containing detectable amounts of formaldehyde are within the scope of this invention.

BRIEF DESCRIPTION OF THE DRAWING

The Figure is a graph showing color ratings of an oxazole-containing ACRN sample to which was added 0.4% of water vs. an analogous sample to which was added 0.4% of formaldehyde as a 37% aqueous solution. Ratings, determined after aging times of 14, 61 and 117 days, show that the sample to which formaldehyde was added developed less color than did the sample to which only water was added. The graph is based on data summarized in Example 8.

DETAILS OF THE INVENTION

Processes for the production of ACRN by the vapor phase catalytic reaction of propylene, oxygen and ammonia are well known. A wide variety of catalysts for the process are described in the art. These may include depleted uranium, bismuth phosphomolybdates, as well as complex selenium and tellurium compounds. An overall review of ACRN production is contained in the Kirk-Othmer Encyclopedia of Chemical Technology, 3rd Ed., Vol. 1, pages 414 to 426, Wiley-Interscience, New York, 1978. The most common commercial process is described on pages 417 to 419 of this reference.

In any event, ACRN produced by the above-described or similar processes is often subject to color-formation with time. Oxazole is an impurity in ACRN and the color is believed to be caused by the ACRN-oxazole reaction product. When formaldehyde is added, it is believed that the formaldehyde reacts with oxazole at a rate faster than that between ACRN and oxazole to produce a significantly less colored product. Alternatively, there may be some other mechanism by which formaldehyde inhibits the reaction between ACRN and oxazole.

The more formaldehyde added, the more color stable the oxazole-containing ACRN will be. Since ACRN is usually present in great excess to compete with formaldehyde for reaction with oxazole, it is preferred to use large amounts of formaldehyde. The upper limit on formaldehyde addition is a practical one dependent upon solubility of formaldehyde in ACRN, polymerization properties of formaldehyde-rich ACRN, cost of formaldehyde removal, etc.

For best results in stabilizing against color, a mole ratio of about 8 to 1 and preferably 10 to 1 or more of formaldehyde to oxazole should be used. It is most preferred to employ a ratio of about 20 to 1. It is contemplated that aqueous formaldehyde can be employed as well as dry formaldehyde gas, meta- or para-formaldehyde, or any other formaldehyde-source that is not harmful to ACRN. If aqueous formaldehyde is employed, which is the preferred manner of practicing this invention, the upper limit may well be governed by the solubility of water in ACRN.

The reaction product of oxazole and formaldehyde was identified as follows. A solution of 3 gms of commercial 37% aqueous formaldehyde and 1 gm of oxazole was heated in a sealed vial to 100° C. (boiling water bath) for 6 hrs during which time a dark orange color developed. The vial was opened and the contents evaporated in a vacuum oven to leave a water-soluble, resinous solid. I.R. analysis indicated the solid to have a polymeric structure containing multiple hydroxyl groups similar to some polyformaldehyde resins. No I.R. absorption bands typical of the oxazole ring structure were seen.

A similar experiment was run except that the oxazole was left out, i.e., the vial contained only 37% formaldehyde. After 6 hrs, the vial contents remained water clear and evaporation left only a trace of white residue. The experiment outlined in the preceding paragraph was then repeated with identical results. Thus, it appears that the reaction between oxazole and formaldehyde is one in which the oxazole ring is opened to form a resinous, water-soluble polymer containing multiple hydroxyl groups.

The following Examples illustrate the invention.

EXAMPLES 1 TO 3

Commercial grade 37% aqueous formaldehyde was added to three ACRN solutions each weighing 5.000 gms and containing 200 ppm of oxazole. A fourth 5.000 gm sample of ACRN was kept as control, no formaldehyde being added. Color stability was determined after aging the samples in sealed bottles for 24 hours at 100° C. The calculations, based on an absorption of 360 nanometers wave length radiation in a 1 cm cell, was as follows:

Color Index=(Absorption) (4)(142).

A Color Index value below about 20 indicates an essentially water-white material. Increasingly higher Color Indices indicate an increasing degree of yellowness, and a Color Index of 500 indicates a deep yellow material.

TABLE 1

| Ex. No. | Gms of 37% Aqueous Formaldehyde Added | Wt. Percent Of Water In The Sample | Mole Ratio of Formaldehyde to Oxazole | Color Index After Storage |
| --- | --- | --- | --- | --- |
| Control | 0 | 0 | 0 | 507 |
| 1 | 0.100 | 1.23 | 83 | 68 |
| 2 | 0.050 | 0.62 | 41.5 | 87 |
| 3 | 0.025 | 0.31 | 20.75 | 145 |

COMPARATIVE EXAMPLES A TO D

Samples were prepared and aged in the same manner as were those of Examples 1 to 3 except that pure distilled water was added in place of formaldehyde solution. Color was likewise determined as in Examples 1 to 3. Results are reported in Table 2.

TABLE 2

| Comparative Example | Weight Percent of Water | Color Index |
| --- | --- | --- |
| A | 1.96 | 185 |
| B | 0.99 | 160 |
| C | 0.498 | 170 |
| D | 0.249 | 277 |

The results of Examples A to D when compared with the results of Examples 1 to 3 show that water has relatively little effect on stabilizing against color. Therefore, the primary benefit of stabilization against color is attributable to the presence of formaldehyde.

EXAMPLE 4

Commercial, polymer-grade ACRN containing about 350 ppm of oxazole was tested for color in the manner described in Examples 1 to 3 except that a low-methanol (about 5 weight percent) grade of 37% aqueous formaldehyde was used as the inhibitor. The mole ratio of formaldehyde to oxazole was 18 (0.278 weight percent of formaldehyde in sample) and the color was 181 after aging according to the procedure of Examples 1 to 3.

EXAMPLES 5 AND 6

Two samples were prepared as in Example 4 and tested for color in the manner described in Examples 1 to 3 except that aging was at 60° C. for 7 days. Results are reported in Table 3.

TABLE 3

| Example | Wt. Percent of Formaldehyde | Mole Ratio of Formaldehyde/Oxazole | Color Index |
| --- | --- | --- | --- |
| 5 | 0.37 | 24 | 6 |
| 6 | 0.185 | 12 | 15 |

EXAMPLE 7 AND COMPARISON E

Two samples of 100 g each were prepared as in Example 4 and aged at 60° C. for 6 days in sealed bottles except that one contained formaldehyde and the other only water. Color was tested as in Examples 1 to 3. The results are reported in Table 4.

TABLE 4

| Example | Wt. Percent of Formaldehyde | Mole Ratio of Formaldehyde/Oxazole | Wt. Percent of Water | Color Index |
| --- | --- | --- | --- | --- |
| 7 | 0.185 | 12 | 0.315 | 11 |
| E | 0 | 0 | 0.5 | 63 |

A Color Index of about 15 or less means that little if any color is detectable by the eye. Based on Examples 6 and 7 it is predicated that a mole ratio of about 12 to 1 or higher, formaldehyde to oxazole, will give replicable stable solutions within the meaning of this invention. Examples 6 and 7 describe accelerated aging tests by which the efficacy of various formaldehyde/oxazole ratios can be adjudged. The more useful test is that of Example 6 wherein aging was conducted at 60° C. for 7 days.

EXAMPLE 8 AND COMPARISON F

This Example demonstrates the effectiveness of formaldehyde as a color inhibitor for oxazole-containing acrylonitrile. Tests were run on a formaldehyde-containing sample vs. an analogous sample containing water in place of formaldehyde. The tests, run as described hereafter, are summarized in Table 5.

A 50 gm sample of acrylonitrile containing 320 ppm of oxazole (0.016 gm), 40 ppm (0.002 gm) of hydroquinone polymerization inhibitor and 0.4% of water (0.2 gm) was weighed into a screw-cap bottle. A similar sample was weighed into an identical bottle except that 0.4% (0.2 gm) of 37% commercial formaldehyde solution was substituted for the water. The mole ratio of formaldehyde to oxazole was 10.6. Both bottles were immersed in a constant-temperature bath maintained at 35° C.

TABLE 5

| | Color Index | | |
| --- | --- | --- | --- |
| Example | 14 days | 61 days | 117 days |
| F (0.4% water) | 24 | 91 | 256 |
| 8 (0.4% formaldehyde; 37% solution) | 11 | 18 | 56 |

The data obtained in this comparison were plotted and form the basis for the Figure.

The embodiments of the invention in which an exclusive property or privilege is claimed are defined as follows:

1. A process for stabilizing oxazole-containing acrylonitrile prepared by the ammoxidation of propylene against oxazole-induced color formation, comprising adding thereto an effective color-inhibiting amount of formaldehyde.

2. A process according to claim 1 comprising adding the formaldehyde in a mole ratio of at least about 1 to 1, formaldehyde to oxazole.

3. A process according to claim 2 comprising adding the formaldehyde in a mole ratio of at least about 8 to 1, formaldehyde to oxazole.

4. A process according to claim 3 comprising adding the formaldehyde in a mole ratio of at least about 10 to 1, formaldehyde to oxazole.

5. A process according to claim 1 comprising adding the formaldehyde in the form of an aqueous solution.

6. A process according to claim 2 comprising adding the formaldehyde in the form of an aqueous solution.

7. A process according to claim 3 comprising adding the formaldehyde in the form of an aqueous solution.

8. A process according to claim 4 comprising adding the formaldehyde in the form of an aqueous solution.

9. A solution composition of oxazole-containing acrylonitrile, prepared by the ammoxidation of propylene, said composition also comprising water and formaldehyde.

10. A solution composition according to claim 9 containing about 0.15 weight percent of formaldehyde and about 0.25 weight percent of water.

* * * * *

UNITED STATES PATENT OFFICE
CERTIFICATE OF CORRECTION

PATENT NO. : 4,211,722
DATED : July 8, 1980
INVENTOR(S) : Robert A. Smiley

It is certified that error appears in the above-identified patent and that said Letters Patent are hereby corrected as shown below:

Column 6, line 3, after formaldehyde change "." to --,-- and add the following:

-- said formaldehyde being present in an amount effective to inhibit oxazole-induced color formation. --

Signed and Sealed this

Twenty-fourth Day of February 1981

[SEAL]

*Attest:*

*Attesting Officer*

RENE D. TEGTMEYER

*Acting Commissioner of Patents and Trademarks*